US00PP37622P2

(12) United States Plant Patent
McBee et al.

(10) Patent No.: US PP37,622 P2
(45) Date of Patent: Aug. 18, 2026

(54) ***DIERVILLA* PLANT NAMED 'Baildiertwo'**

(50) Latin Name: ***Diervilla* X *splendens***
Varietal Denomination: Baildiertwo

(71) Applicant: Bailey Nurseries, Newport, MN (US)

(72) Inventors: Oren McBee, Bishop, GA (US); David Jonathan Roberts, Athens, GA (US); Justin Schulze, Athens, GA (US)

(73) Assignee: BAILEY NURSERIES, INC., Newport, MN (US)

( * ) Notice: Subject to any disclaimer, the term of this patent is extended or adjusted under 35 U.S.C. 154(b) by 0 days.

(21) Appl. No.: 19/366,286

(22) Filed: Oct. 22, 2025

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Diervilla* named 'Baildiertwo' that is characterized by its dark purple foliage that is maintained throughout the growing season, its dense and compact plant habit, its minimal suckering, and its cold hardiness at least in U.S.D.A. Zone 3.

2 Drawing Sheets

Botanical classification: *Diervilla* X *splendens*.
Variety denomination: 'Baildiertwo'.

BACKGROUND OF THE INVENTION

The present invention relates to a new and distinct cultivar of *Diervilla* X *splendens* and will be referred to hereafter by its cultivar name, 'Baildiertwo'. 'Baildiertwo' is a new cultivar of bush honeysuckle grown for use as a landscape plant.

The new cultivar is the result of a controlled breeding program conducted by the Inventors in Watkinsville, Georgia. The goal of the breeding program was to develop a new cultivar of *Diervilla* with dense and compact plant habits, reduced suckering, and dark purple foliage that maintains its color all season.

The new cultivar arose from open pollination in summer of 2019 of an unpatented proprietary plant in the Inventors' breeding program, reference no. DR19-02-08, as the female parent. The male parent is therefore unknown. The Inventors selected 'Baildiertwo' as a single unique plant amongst the seedlings that resulted from the above cross in summer of 2020.

Asexual propagation of the new cultivar was first accomplished by one of the Inventors using softwood stem cuttings in summer of 2020 in Winterville, Georgia. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baildiertwo' as a unique cultivar of *Diervilla*.

1. 'Baildiertwo' exhibits dark purple foliage that is maintained throughout the growing season.
2. 'Baildiertwo' exhibits a dense and compact plant habit.

3. 'Baildiertwo' exhibits minimal suckering.
4. 'Baildiertwo' exhibits cold hardiness at least in U.S.D.A. Zone 3.

The female parent plant of 'Baildiertwo' differs from 'Baildiertwo' in having foliage that changes to bronze-green in the summer, a loose and open plant habit, and a larger plant size. 'Baildiertwo' can be most closely compared to *Diervilla* cultivars 'El Madrigal' (U.S. Plant Pat. No. 28,060), and 'SMNDRSF' (U.S. Plant Pat. No. 27,550). Both 'El Madrigal' and 'SMNDRSF' are similar to 'Baildiertwo' in having new foliage that is purple in color and yellow flowers. 'El Madrigal' differs from 'Baildiertwo' in having foliage that fades to bronze green in summer and a more open plant habit, and in spreading rapidly by suckering. 'SMNDRSF' differs from 'Baildiertwo' in having foliage that is dark green in summer, a larger plant size, and less cold hardiness.

BRIEF DESCRIPTION OF THE DRAWINGS

The accompanying colored photographs illustrate the overall appearance and distinct characteristics of the new *Diervilla*. The photographs were taken of five year-old plants of the new cultivar as grown outdoors in a trial plot in Newport, Minnesota.

The photograph in FIG. 1 was taken of numerous plants in a trial plot and provides a view of the plant habit and foliage coloration of 'Baildiertwo'.

Figure 1:
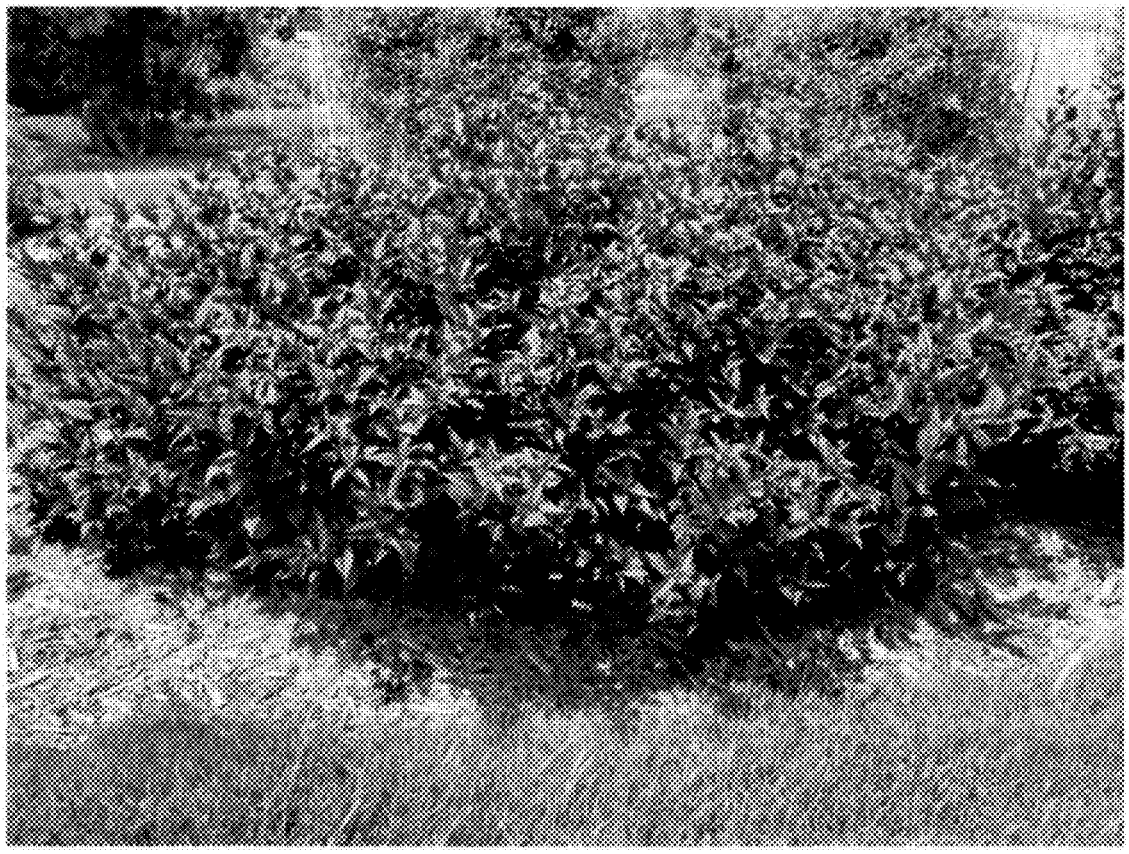
Figure 2:
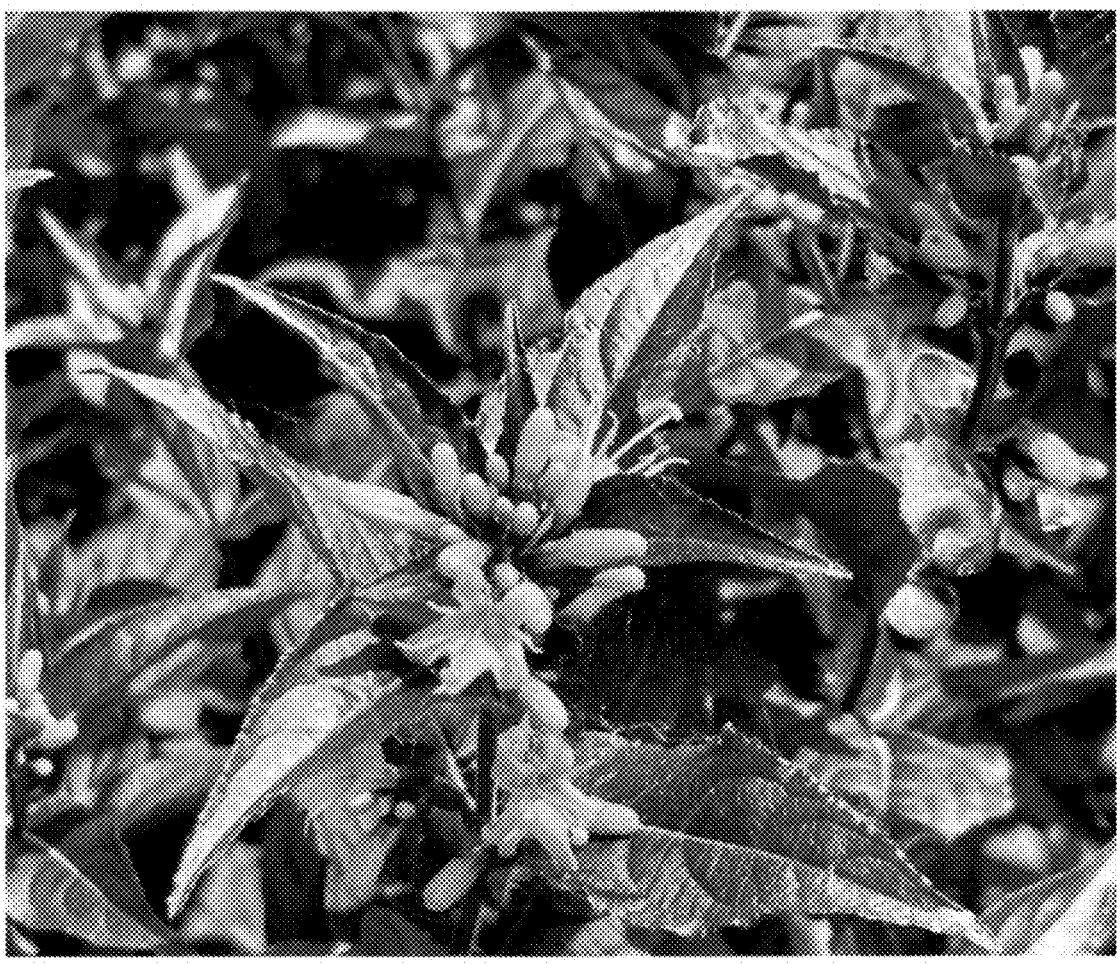

The photograph in FIG. 2 is a close-up view of an opening inflorescence of 'Baildiertwo'.

The colors in the photographs are as close as possible with the digital photography techniques available, the color values cited in the detailed botanical description accurately describe the colors of the new *Diervilla*.

DETAILED BOTANICAL DESCRIPTION

The following is a detailed description of one year-old plants of the new cultivar as grown outdoors in 2-gallon containers in Newport, Minnesota. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—Blooms from June to September in Newport, Minnesota.

*Plant habit*.—Compact and dense.

*Plant type*.—Perennial, deciduous shrub.

*Height and spread*.—Average of 55 cm in height and 75 cm in width as a one-year-old plant grown in a container, reaches an average of 1.2 m in height and width as grown in the landscape.

*Cold hardiness*.—At least in U.S.D.A. Zone 3.

*Disease and pests*.—No susceptibility or resistance to diseases or pests has been observed.

*Propagation*.—Softwood stem cuttings.

*Root description*.—Fibrous.

*Root development*.—Roots initiate in 25 days and fully develop as a young rooted plant in 45 days.

*Growth rate*.—Moderate.

Branch description:

*Branch shape*.—Quadangular.

*Branch color*.—Young; a blend of 149A and 145C, then becoming flushed with 184A, mature; 187A.

*Branch size*.—An average of 35 cm in length and 3 cm in diameter.

*Branch surface*.—Young; slightly glossy and moderately covered with soft pubescent hairs that match surface color, mature; moderately to densely covered with soft pubescent hairs that either match the surface color or are NN155D in color.

*Branch aspect*.—Held upright to slightly outward.

*Branch strength*.—Young; strong and bendable, mature; strong.

*Internode length*.—Average of 4 cm.

*Branching habit*.—An average of 30 branches emerging from base.

Foliage Description:

*Leaf shape*.—Lanceolate to elliptical.

*Leaf division*.—Simple.

*Leaf base*.—Truncate.

*Leaf apex*.—Apiculate.

*Leaf venation*.—Pinnate, upper surface; 181A, lower surface; 176A.

*Leaf margins*.—Serrate.

*Leaf arrangement*.—Opposite.

*Leaf attachment*.—Petiolate.

*Leaf surface*.—Upper surface; rugose, glabrous and matte with a very slight sheen, lower surface; rugose, glabrous and very sheen, main vein is densely covered with adpressed soft pubescent hairs that either match the vein color or are NN155C in color.

*Leaf size*.—Average of 9 cm in length and 3.5 cm in width.

*Leaf quantity*.—Average of 20 leaves per branch.

*Leaf color*.—Young and mature upper surface; NN137A with a heavy overlay of N186A, young and mature lower surface; 148B.

*Petioles*.—Average of 4 mm in length, 2 mm in width, both surfaces moderately glossy and pubescent, color; upper surface 145D, lower surface 177A.

*Stipules*.—None present.

Inflorescence Description:

*Inflorescence type*.—Terminal and axillary compound cymes of tubular flowers.

*Inflorescence size*.—Average of 2 cm in height and 2.5 cm in width.

*Flower fragrance*.—None.

*Lastingness of inflorescence*.—Average of one week, self-cleaning.

*Flower quantity*.—Average of 30 flowers per stem, 8 per inflorescence, inflorescences produced through the growing season.

*Flower type*.—Single, campanulate with tubular base.

*Flower size*.—Average of 2.5 cm in depth and 1.5 cm in diameter.

*Flower aspect*.—Upright to outward, en masse whorled.

*Flower buds*.—Narrow oblong in shape, an average of 1.7 cm in length and 3 mm in width, 145A in color, glossy and glabrous surfaces.

*Peduncles*.—1.5 cm in length and 1 mm in diameter, strong, held at an average angle of 30° to soil level, 144C in color, surface texture glabrous, round in shape.

*Pedicels*.—2.5 mm in length and 1 mm in diameter, moderately strong, held in an average angle of 20° to peduncle, 144C in color, glabrous surface, round in shape.

*Calyx*.—Rotate in shape, average of 2.5 mm in length and 2 mm in diameter, glabrous surface.

*Sepals*.—5, lanceolate in shape, narrow acuminate apex, base fused and cuneate, glabrous and matte on both surfaces, entire margin, average of 2 mm in length and 0.5 mm in width, color of both surfaces 144C.

*Petals*.—5, rotate with 5 lobes with lower 50% of petal fused into tube, both surfaces are glabrous, matte and slightly rugose with lower lobe moderately covered with dense soft hairs; 0.5 mm in length, NN155D in color, lobes; linear in shape, margins entire and slightly undulate, acute apex, average of 6 mm in length and 2 mm in width, color: upper lobes upper and lower surface when opening and fully open; 149A and can become suffused with N34B on upper surface, lower lobe both surfaces 14A and can become suffused with N34B on upper surface, tube; average of 3 mm in length and 3 mm in width, both surfaces 149A in color and can become suffused with N34B on outer surface, both surfaces are matte and glabrous.

Reproductive Organs:

*Gynoecium*.—Pistil; 1, style; 1.5 cm in length and 150B in color, stigma; 0.5 mm in diameter, club-shape, 150B in color, ovary; 146D in color.

*Androecium*.—Stamens; 5, filaments; 145C in color and 1 cm in length, anthers; 5 mm in length and 164B in color, dorsifixed, pollen is moderate and 164B in color.

*Fruit and seed*.—No fruit or seed has been observed to date.

It is claimed:

1. A new and distinct cultivar of *Diervilla* plant named 'Baildiertwo' as herein illustrated and described.

* * * * *